Figure 1:
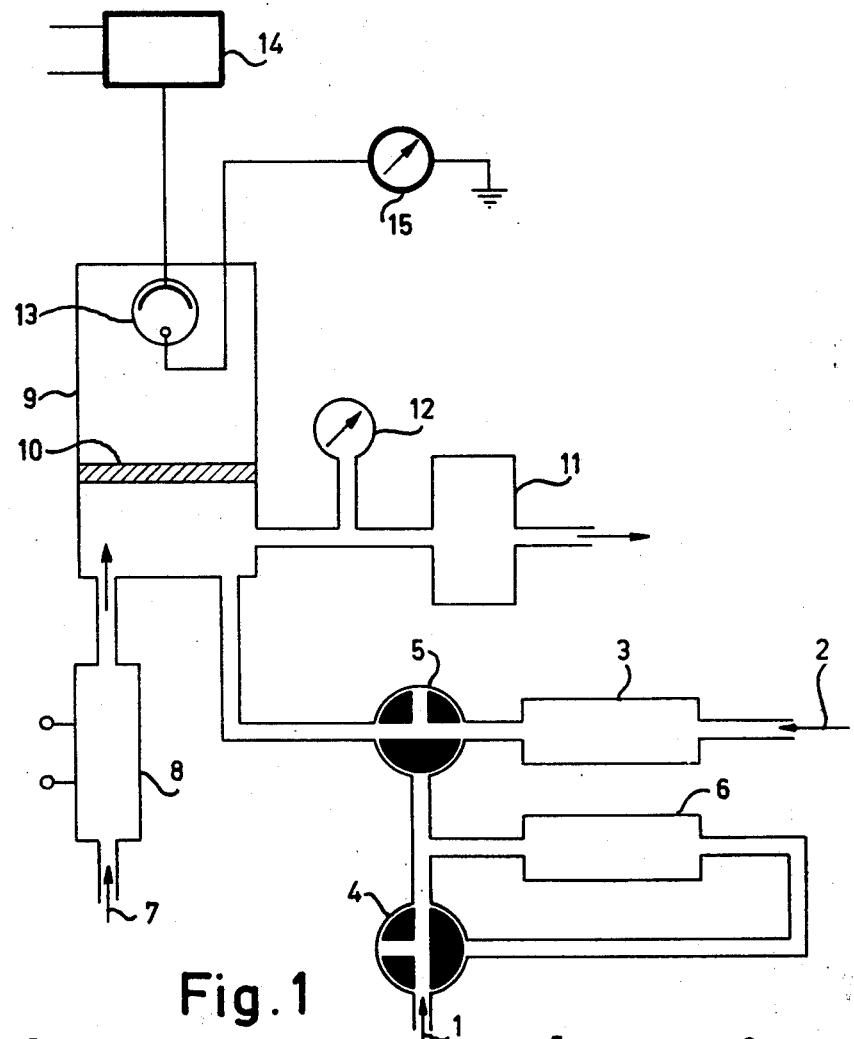

United States Patent [19]
van Heusden

[11] 3,973,914
[45] Aug. 10, 1976

[54] APPARATUS FOR THE DETERMINATION OF NITROGEN OXIDES IN AIR

[75] Inventor: Sybrandus van Heusden, Eindhoven, Netherlands

[73] Assignee: U.S. Philips Corporation, New York, N.Y.

[22] Filed: Dec. 3, 1974

[21] Appl. No.: 529,123

[30] Foreign Application Priority Data
Jan. 31, 1974 Netherlands.................... 7401320

[52] U.S. Cl. ............................. 23/254 E; 252/188; 423/405
[51] Int. Cl.² ................. G01N 31/00; C01B 21/24; C09K 3/00
[58] Field of Search ....... 252/188; 23/254 E, 232 E, 23/281; 423/405

[56] References Cited
UNITED STATES PATENTS
3,659,100   4/1972   Anderson et al.................. 23/252 R
3,870,468   3/1975   Neti.................................. 423/405

OTHER PUBLICATIONS
Paterson et al., "A Prototype Chemiluminescent NO Analyzer", Univ. of Cal., Dept. Mech. Eng., Thermal Systems Div. Report, Sept. 1970, pp. 7–12.

Stuhl et al., "An Optical Detection Method for NO . . . by the Chemiluminescent Reaction of NO With $O_3$", Scientific Research Staff, Ford Motor Co. Tech. Report SR70-42, Mar. 1970, Fig. I.

"Quantitative Measurement of Nitrogen Dioxide in Gaseous Mixtures", Anal. Abst., vol. 27, Abst. 1070, Aug. 1974.

"Quantitative Measurement of Ammonia in Gaseous Mixtures", Anal. Abst., vol. 27, Abst. 1071, Aug. 1974.

*Primary Examiner*—Joseph Scovronek
*Assistant Examiner*—Barry I. Hollander
*Attorney, Agent, or Firm*—Frank R. Trifari; Norman N. Spain

[57] ABSTRACT

A mixture of ferrous sulphate and alkali metal acid sulphate used in a reducer employed for converting $NO_2$ to NO in an apparatus for determining the nitrogen oxide content of air by means of the measurement of the reaction of ozone and NO.

2 Claims, 3 Drawing Figures

APPARATUS FOR THE DETERMINATION OF NITROGEN OXIDES IN AIR

In copending U.S. Pat. application Ser. No. 529,124 filed Dec. 3, 1974 (corresponding with Dutch Patent Application 7316555, filed December 4th, 1973) an apparatus for the chemical conversion of gas mixtures, is described which comprises a container having an inlet and an outlet and filled with a granular ferrous sulphate composition and which is characterized in that the composition is a mixture of ferrous sulphate and an alkali metal acid sulphate in a molar ratio from 3:1 to 1:1, which mixture is preferably applied to the surface of an inert carrier-material.

The present invention relates to an important use of the said apparatus, i.e. an apparatus for simultaneously determining the amounts of nitrogen monoxide and nitrogen dioxide in air by means of the chemiluminescence reaction between NO and $O_3$.

This reaction is known, see inter alia a paper by A. Fontijn, A. J. Sabadell and R. J. Ronco in J. Anal. Chem. 42, 575–579 (1970). The reaction energy is delivered in the form of radiation in the wavelength range above 600 nm. The intensity of this light is measured by means of a photomultiplier tube. In front of this photomultiplier tube a reaction vessel is disposed in which air which contains NO is mixed with a large excess of gaseous ozone. The ozone is obtained from air or oxygen by means of a dark discharge. The reaction is preferably carried out at a pressure of about 2 torr, because otherwise a large part of the excited $NO_2$ molecules in the reaction equation

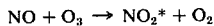

cannot deliver its energy in the form of radiation. Another difficulty is due to the fact that the commercially available photomultiplier tubes have a low sensitivity above 600 nm. Hence these tubes have to be used at a low temperature (of about $-20°C$) to diminish the influence of the dark current when measuring concentrations of the order of $10^{-7}$ per cent (p.p.b.).

In a paper "Gas sampling and analysis in combustion phenomena" by G. Lengelle and C. Verdier of the Advisory Group for Aerospace Research and Development, AGARDograph No. 168, July 1973, pages 176 and 177, an apparatus is described by means of which the amounts of NO and $NO_x = NO + NO_2$, calculated as NO, can be determined by means of the said chemiluminescence reaction. The conversion of $NO_2$ into NO is effected in the apparatus described by means of a coil heated above $650°C$. However, because of the comparatively small reaction area the said conversion requires a comparatively long dwell of the gas, which means that instantaneous measurement is not well possible. Hence alternate measurements of NO and $NO_x$ require long measuring times. Consequently, to suppress the variations in dark current the photomultiplier tube must be operated at a low temperature, as mentioned hereinbefore.

The use of the reductor as described above permits considerable simplification of the known apparatus, because conversion is quantitative and the conversion rate is very high. In addition, the reductor has a long useful life of about 3 months. This means that the concentrations of NO and $NO_x$ can alternately be determined in a few seconds, so that the influence of variations in the dark current of the photomultiplier tube is greatly diminished and the tube can be operated at the ambient temperature.

The apparatus according to the invention comprises an ozoniser which supplies a constant stream of ozone and a reaction chamber which contains a photomultiplier for measuring the luminescence emission of the reaction of nitrogen monoxide and ozone, into which chamber a gas conduit opens which through a valve can at will admit either air containing no nitrogen oxide or air to be analysed, whilst the latter gas stream can be supplied via a valve either directly or via a reductor, and the apparatus according to the invention is characterized in that the reductor is of the type comprising a container which has an inlet and an outlet and is filled with a granular composition which comprises ferrous sulphate and an alkali metal acid sulphate in a molar ratio between 3:1 and 1:1 and preferably is applied to the surface of an inert carrier material.

The invention is illustrated with the aid of a drawing.

FIG. 1 shows an embodiment of the device according to the invention, in which 1 is an inlet for air to be analyzed and an inlet 2 through which air from which nitrogen oxide is removed by a filter 3 is passed for setting the zero point. The apparatus further has three-way valves 4 and 5 which in the position shown in FIG. 1 enable the zero point to be determined.

Figures 2, 3:
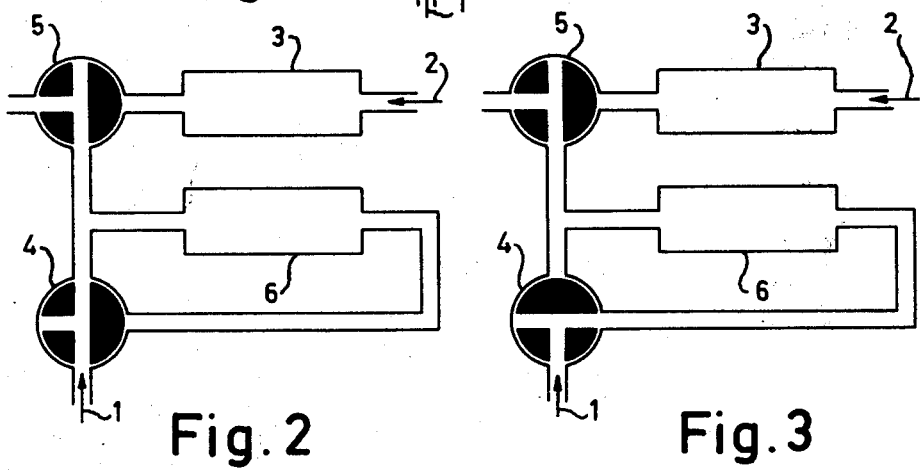

FIG. 2 shows part of the apparatus of FIG. 1, with the three-way valves 4 and 5 in the positions in which the proportion of NO is determined, and FIG. 3 shows part of the apparatus of FIG. 1 with the three-way valves in the positions in which the proportion of $NO + NO_2$, calculated as NO, is determined. In one embodiment the reductor 6 is filled with grains of pumice coated with $FeSO_4$ and $KHSO_4$ in a molar ratio of 1:1.

The determination of the NO is effected by photometric determination of the emitted light of chemiluminescence produced in a chamber 9 by the reaction of NO and ozone. The reaction light passes through an optical filter 10, by which the radiation below 600 nm is absorbed, and strikes a photomultiplier tube 13 which is fed by a high-voltage unit 14. The photocurrent which is measured by an ammeter 15 is a measure of the proportion of NO. The ozone is supplied by an ozonizer 8 which takes in pure air or oxygen 7 and in which a dark discharge is maintained at an alternating voltage of about 6 kV. The flow of air through chamber 9 is controlled by pump 11 and manometer 12.

What is claimed is:

1. In an apparatus for simultaneously determining the amounts of nitrogen monoxide and nitrogen dioxide in air by means of an apparatus comprising an ozonizer suitable for supplying a continuous stream of ozone, a reaction chamber positioned to receive ozone from said ozonizer and air containing nitrogen oxide or air free of nitrogen oxide and containing a photomultiplier for measuring the luminescence emission of the reaction between nitrogen monoxide and ozone, a conduit connecting said ozonizer to said reaction chamber for transferring said ozone to said reaction chamber, a gas conduit opening into said reaction chamber containing a valve suitable for admitting air free of nitrogen oxide or air to be analyzed through said conduit opening into said reaction chamber, a reducer connected to said valve for reducing nitrogen dioxide in the air to be analyzed to nitrogen monoxide and a valved by-passing conduit for by-passing the reducer the improvement wherein said reducer comprises a container having an inlet and an outlet and is filled with a granular mixture of ferrous sulphate and an alkali metal acid sulphate in a molar ratio of from 3:1 to 1:1.

2. The apparatus of claim 1 wherein the granular mixture is carried on the surface of an inert carrier material.

* * * * *